US012597188B2

(12) United States Patent
Hahn, III et al.

(10) Patent No.:  US 12,597,188 B2
(45) Date of Patent:      Apr. 7, 2026

(54) SYSTEMS AND METHODS FOR PROCESSING ELECTRONIC IMAGES FOR PHYSIOLOGY-COMPENSATED RECONSTRUCTION

(71) Applicant: HeartFlow, Inc., Redwood City, CA (US)

(72) Inventors: Edward Karl Hahn, III, Foster City, CA (US); Michiel Schaap, Oegstgeest (NL); Daniel Rueckert, Munich (DE)

(73) Assignee: Heartflow, Inc., Mountain View, CA (US)

( * ) Notice: Subject to any disclaimer, the term of this patent is extended or adjusted under 35 U.S.C. 154(b) by 378 days.

(21) Appl. No.: 18/059,154

(22) Filed: Nov. 28, 2022

(65) Prior Publication Data

US 2023/0169702 A1      Jun. 1, 2023

Related U.S. Application Data

(60) Provisional application No. 63/283,630, filed on Nov. 29, 2021.

(51) Int. Cl.
*G06T 11/00* (2006.01)
*A61B 6/03* (2006.01)
*G06T 7/00* (2017.01)

(52) U.S. Cl.
CPC ............ *G06T 11/003* (2013.01); *A61B 6/032* (2013.01); *G06T 7/0012* (2013.01); *G06T 2207/30048* (2013.01)

(58) Field of Classification Search
CPC ......... A61B 6/032; A61B 6/466; A61B 6/469;
A61B 6/5217; A61B 6/5258; A61B 6/12;
G06T 11/005; G06T 11/008; G06T
7/0012; G06T 5/00; G06T 2207/10116;
G06T 2207/10081; G06T 11/00; G06T
2207/10072; G06T 2207/10124; G06T
2207/10088; G06T 2207/30004; G06T
2207/30052; G06T 2210/41; G06T 5/50;
G06T 7/0014; G06T 2211/424; G16H
50/50

See application file for complete search history.

(56) References Cited

U.S. PATENT DOCUMENTS 6,765,983 B2 *  7/2004  Yan ...................... A61B 6/5264
                                                        378/8
7,369,695 B2 *  5/2008  Zettel ........................ G06T 5/70
                                                        378/4

(Continued)

FOREIGN PATENT DOCUMENTS

EP              1627601 A1      2/2006

*Primary Examiner* — Courtney Joan Nelson
(74) *Attorney, Agent, or Firm* — Bookoff McAndrews, PLLC

(57) ABSTRACT

A computer-implemented method for medical measurement reconstruction may comprise: receiving a measurement acquisition signal; based on the received measurement acquisition signal, creating a plurality of representations of the measurement acquisition signal, wherein each of the plurality of representations relates to a different aspect of the measurement acquisition signal; modifying one or more of the plurality of representations; and generating an output signal including the modified one or more of the plurality of representations.

20 Claims, 7 Drawing Sheets

(56)                    References Cited

U.S. PATENT DOCUMENTS

| | | | |
|---|---|---|---|
| 7,782,998 B2 * | 8/2010 | Langan | G01N 23/046 |
| | | | 378/8 |
| 8,891,847 B2 * | 11/2014 | Helm | G06T 19/20 |
| | | | 382/131 |
| 8,917,925 B1 | 12/2014 | Grady et al. | |
| 9,022,933 B2 * | 5/2015 | Hsieh | A61B 6/4417 |
| | | | 600/407 |
| 9,317,661 B2 * | 4/2016 | Helm | G06T 7/0014 |
| 10,789,706 B2 | 9/2020 | Grady et al. | |
| 2014/0023290 A1 * | 1/2014 | Barth | G06T 11/005 |
| | | | 382/275 |
| 2014/0328450 A1 * | 11/2014 | Pal | A61B 6/032 |
| | | | 378/20 |
| 2015/0366525 A1 * | 12/2015 | Sandholm | A61B 6/4085 |
| | | | 378/4 |
| 2018/0182096 A1 | 6/2018 | Grady et al. | |

* cited by examiner

400

402 RECEIVE ACQUISITION SIGNAL(S)

404 RECONSTRUCT IMAGE USING ESTIMATE OF DYNAMIC(S)

406 PARTITION IMAGE INTO BODY LUMEN AND BACKGROUND

408 ESTIMATE ATTENUATION MAP

410 MODIFY BACKGROUND ATTENUATION MAP

412 CONDITION(S) SATISFIED?

418 NO

414 YES

416 GENERATE AT LEAST ONE SIGNAL

502 RECEIVE ACQUISITION SIGNAL(S)

504 RECONSTRUCT IMAGE USING ESTIMATE OF DYNAMIC(S)

506 PARTITION IMAGE INTO CARDIAC CHAMBERS AND BACKGROUND

508 ESTIMATE CARDIOTHORACIC MOTION FIELD

510 CONDITION(S) SATISFIED?

516 NO

512 YES

514 GENERATE AT LEAST ONE SIGNAL

500

602 RECEIVE ACQUISITION SIGNAL(S)

604 RECONSTRUCT IMAGE USING ESTIMATE OF DYNAMIC(S)

606 PARTITION IMAGE INTO CORONARY LUMEN, CARDIAC CHAMBER(S), AND/OR BACKGROUND

608 ESTIMATE MYOCARDIAL TERRITORIES AND/OR FLOW OF CONTRAST AGENT

610 ESTIMATE MYOCARDIAL ATTENUATION MAP

612 MODIFY BACKGROUND ATTENUATION MAP

614 CONDITION(S) SATISFIED?

620 NO

616 YES

618 GENERATE AT LEAST ONE SIGNAL

600

SYSTEMS AND METHODS FOR PROCESSING ELECTRONIC IMAGES FOR PHYSIOLOGY-COMPENSATED RECONSTRUCTION

CROSS-REFERENCE TO RELATED APPLICATION[S]

This application claims priority to U.S. Provisional Application No. 63/283,630, filed Nov. 29, 2021, which is incorporated herein by reference in its entirety.

TECHNICAL FIELD

Embodiments include methods and systems for image reconstruction and, more particularly, methods and systems for physiology-compensated reconstruction.

BACKGROUND

Medical imaging pipelines may collect measurements and produce images of subject anatomy reconstructed from the measurements. The reconstructed images may be used by downstream tasks. Such downstream tasks may include, for example, analysis and/or interpretation. Analysis may include, for example, creation of model(s) and/or simulation(s). Existing reconstruction methods may assume that a subject is motionless throughout the acquisition. Such assumption may produce errors in the reconstruction. Therefore, a need exists for methods and systems for physiology-compensated reconstruction.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the disclosure, systems and methods are disclosed for incorporating user inputs in a medical imaging pipeline.

In an example, a computer-implemented method for medical measurement reconstruction may comprise: receiving a measurement acquisition signal; based on the received measurement acquisition signal, creating a plurality of representations of the measurement acquisition signal, wherein each of the plurality of representations relates to a different aspect of the measurement acquisition signal; modifying one or more of the plurality of representations; and generating an output signal including the modified one or more of the plurality of representations.

Any of the methods, systems, or devices disclosed herein may include any of the following features. The output signal may include a reconstruction of the measurement acquisition signal or wherein the output signal is used to generate a reconstruction of the measurement acquisition signal. The measurement acquisition signal may include a medical imaging signal. The plurality of representations may include a representation of at least one of anatomy, motion, or a physiological process. The plurality of representations may be created based on known information about the at least one of the anatomy, the motion, or the physiological process. The method may further comprise determining whether a stop condition is satisfied and, upon determining the stop condition is not satisfied, iterating at least one of the receiving, the creating, the modifying, or the generating step. The method may further comprise reconstructing an image using an estimate of dynamics. The plurality of representations may include at least one of a body lumen, an attenuation map, a cardiac chamber, a cardiothoracic motion field, a myocardial territory, or a flow of contrast agent. The method may further comprise modifying the representation based on a presence of an implanted hardware. The modifying the one or more of the plurality of representations may address an artifact in the measurement acquisition signal.

In another example, a system for processing electronic images for medical measurement reconstruction may comprise: a data storage device storing instructions for medical measurement reconstruction; and a processor configured to execute the instructions to perform operations comprising: receiving a measurement acquisition signal; based on the received measurement acquisition signal, creating a plurality of representations of the measurement acquisition signal, wherein each of the plurality of representations relates to a different aspect of the measurement acquisition signal; modifying one or more of the plurality of representations; and generating an output signal including the modified one or more of the plurality of representations.

In a further example, a non-transitory computer-readable medium may store instructions that, when executed by one or more processors, cause the one or more processors to perform computer-implemented method for medical measurement reconstruction, the method comprising: receiving a measurement acquisition signal; based on the received measurement acquisition signal, creating a plurality of representations of the measurement acquisition signal, wherein each of the plurality of representations relates to a different aspect of the measurement acquisition signal; modifying one or more of the plurality of representations; and generating an output signal including the modified one or more of the plurality of representations.

Additional objects and advantages of the techniques presented herein will be set forth in part in the description that follows, and in part will be apparent from the description, or may be learned by practice of the techniques presented herein. The objects and advantages of the techniques presented herein will be realized and attained by means of the elements and combinations particularly pointed out in the appended claims.

It is to be understood that both the foregoing general description and the following detailed description are exemplary and explanatory only and are not restrictive of the disclosure.

BRIEF DESCRIPTION OF THE DRAWINGS

The accompanying drawings, which are incorporated in and constitute part of this specification, illustrate various exemplary embodiments and together with the description, serve to explain the principles of the disclosed embodiments.

DETAILED DESCRIPTION

Figure 1:
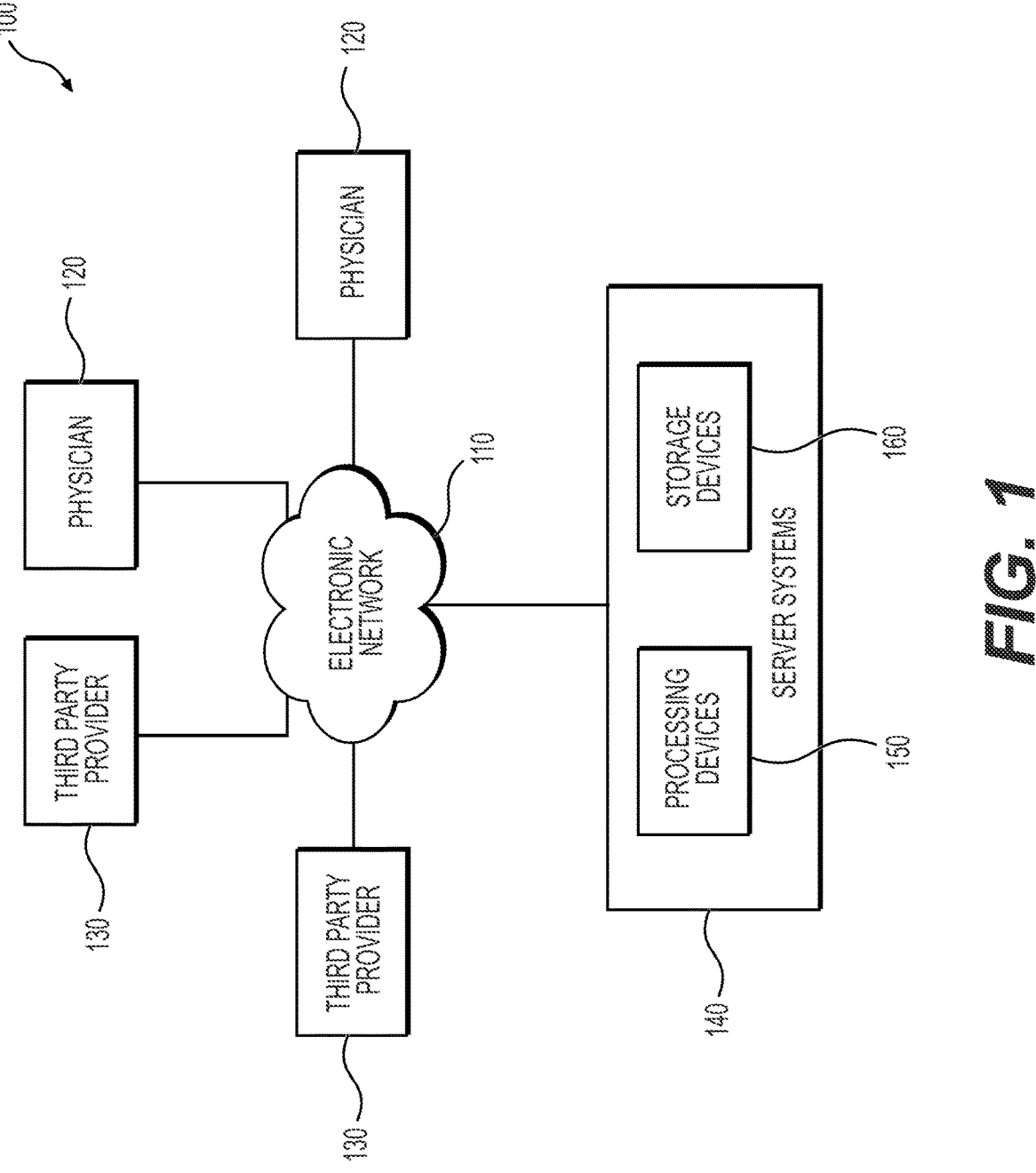
FIG. 1 depicts a computer environment for performing the techniques described herein.

Medical imaging (or other medical measurement gathering) may involve acquiring data using medical imaging equipment. For example, medical imaging modalities may include computed tomography ("CT") (such as, for example, coronary computed tomography angiography ("CCTA")). magnetic resonance imaging ("MRI"), positron emission tomography ("PET"), ultrasound, electrocardiography, and/ or X-ray, or any combination thereof. Data may be acquired using various acquisition protocols, to be selected by a user. Acquired data may be reconstructed in order to transform the data into an image that is interpretable by a human. Such images may be analyzed and/or interpreted by a user or an automated computer system. A medical imaging pipeline may include any of the steps above (acquisition, reconstruction, analysis, and/or interpretation), as well as any other steps.

Sufficient reconstruction quality may be needed for downstream tasks to execute successfully. Reconstruction quality may be degraded by, for example, reconstruction artifacts, which may result from violations of reconstruction method assumptions by processes concurrent with the acquisition. A source of reconstruction artifacts may be patient physiology, including time-dependent changes in patient anatomy. Conventional reconstruction methods may assume infinite temporal resolution of the imaging system: the acquired measurements (and reconstructions thereof) may correspond to the patient anatomy at an instant in time, essentially independent of physiology.

However, imaging system temporal resolution may be finite, and the acquisition may occur over a period of time during which concurrent physiological processes may significantly alter anatomical configuration. For example, cardiac motion may occur during acquisition of measurements. Consequently, influences of anatomy and physiology may become entangled in the acquired measurements, and the instantaneous acquisition assumption may be violated, which may lead to reconstruction artifacts.

Compensation of the influences of these processes may be performed by an approach in which a reconstruction method may mitigate or eliminate corresponding reconstruction artifacts. For example, prior knowledge and/or estimation of subject motion (e.g., cardiac motion) during the acquisition may be used to mitigate appearance of image artifacts otherwise due to that motion. Systems and methods described herein may provide a system or method that compensates for cardiac motion using known, patient-specific cardiac physiology. For example, certain embodiments may provide a system or method that accounts for medical image acquisition and reconstruction artifacts due primarily to subject physiology, such as cardiac motion. Such artifacts may degrade reconstruction accuracy and may introduce uncertainty in downstream applications. Embodiments of the disclosure may include application of knowledge of subject physiology to mitigate this uncertainty. Certain embodiments may be used in connection with certain embodiments disclosed in U.S. patent application Ser. No. 15/852,183, filed Dec. 22, 2017 and published as U.S. Patent Application Publication No. 2018/0182096, which is incorporated herein by reference in its entirety.

In some examples, physiology-compensated reconstruction methods may eliminate an assumption of infinite temporal resolution and may reformulate the reconstruction problem as one of isolating the independent influences of anatomy and physiology, thereby addressing/eliminating a source of corresponding reconstruction artifacts. Isolation may be enabled by incorporating prior knowledge of each factor that allows the influence of one factor to be estimated independently of the others. The disclosed systems and methods for physiology-compensated computed tomography reconstruction utilize prior knowledge of cardiac anatomy, motion, and/or one or more other physiological processes concurrent with the acquisition.

FIG. 1 depicts an example of an environment 100 in which such a computer system may be implemented as server systems 140. In addition to server systems 140, the environment of FIG. 1 further includes a plurality of physicians 120 and third party providers 130, any of which may be connected to an electronic network 110, such as the Internet, through one or more computers, servers, and/or handheld mobile devices. In FIG. 1, physicians 120 and third party providers 130 may each represent a computer system, as well as an organization that uses such a system. For example, a physician 120 may be a hospital or a computer system of a hospital.

Physicians 120 and/or third party providers 130 may create or otherwise obtain medical images, such as images of the cardiac, vascular, and/or organ systems, of one or more patients. Physicians 120 and/or third party providers 130 may also obtain any combination of patient-specific information, such as age, medical history, blood pressure, blood viscosity, and other types of patient-specific information. Physicians 120 and/or third party providers 130 may transmit the patient-specific information to server systems 140 over the electronic network 110.

Server systems 140 may include one or more storage devices 160 for storing images and data received from physicians 120 and/or third party providers 130. The storage devices 160 may be considered to be components of the memory of the server systems 140. Server systems 140 may also include one or more processing devices 150 for processing images and data stored in the storage devices and for performing any computer-implementable process described in this disclosure. Each of the processing devices 150 may be a processor or a device that include at least one processor.

In some embodiments, server systems 140 may comprise and/or utilize a cloud computing platform with scalable resources for computations and/or data storage, and may run an application for performing methods described in this disclosure on the cloud computing platform. In such embodiments, any outputs may be transmitted to another computer system, such as a personal computer, for display and/or storage.

Other examples of computer systems for performing methods of this disclosure include desktop computers, laptop computers, and mobile computing devices such as tablets and smartphones.

A computer system, such as server systems 140, may include one or more computing devices. If the one or more processors of the computer system is implemented as a plurality of processors, the plurality of processors may be included in a single computing device or distribute among a plurality of computing devices. If a computer system comprises a plurality of computing devices, the memory of the computer system may include the respective memory of each computing device of the plurality of computing devices.

Figure 2:
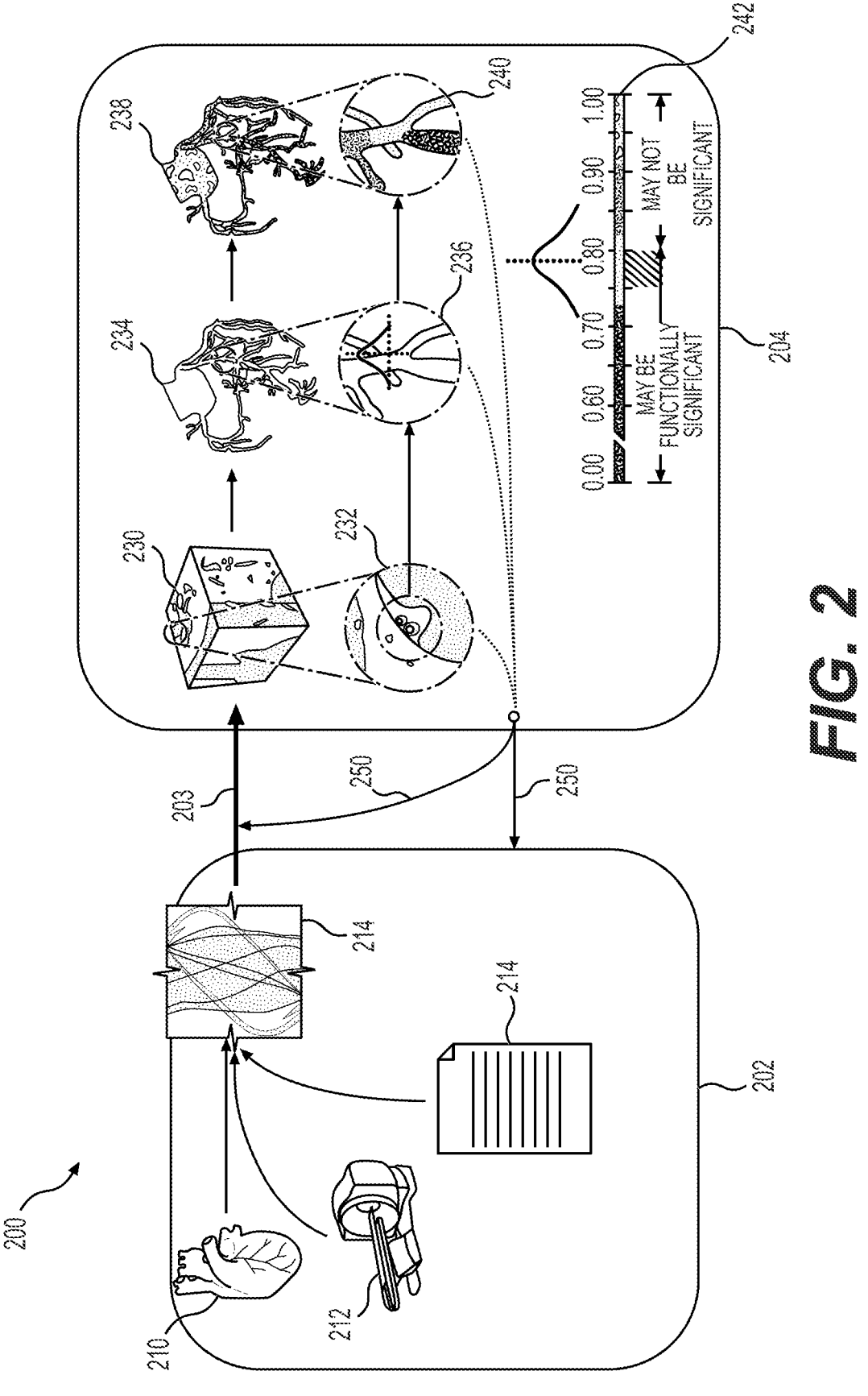
FIG. 2 illustrates an example medical imaging pipeline workflow.

FIG. 2 depicts an exemplary medical imaging workflow 200. Measurements/data may be acquired in acquisition phase 202, and images may be interpreted and analyzed, and user input may be provided, in image phase 204. The arrow extending from acquisition phase 202 to image phase 204 may represent reconstruction of the measurements acquired in acquisition phase 202 into images utilized in image phase 204.

Various factors may contribute to the measurements acquired in acquisition phase 202. Exemplary factors include patient state 210, device properties 212, and preparation protocol 214. Patient state 210 may include various factors, including but not limited to patient position, variabilities in patient anatomy, patient bodily processes (e.g., heartbeats, bloodflow, inhalation/exhalation), patient demographic data, patient physiological characteristics, and/or patient movement. Device properties 212 may include any property of an acquisition device (e.g., scanner). Device properties 212 may include, for example, a modality, a manufacturer, a calibration, and/or measurement collection parameters (e.g., settings). Preparation protocol 214 may include, for example, any steps taken by a patient or medical provider in advance of or during acquisition of the measurements. The patient state 210, device properties 212, and/or preparation protocol 214 (along with other factors) may contribute to the measurements obtained and the projections 216 obtained. The projections may include two-dimensional, projected images/measurements obtained.

As represented by the arrow from acquisition phase 202 to image phase 204, during reconstruction 203, a reconstruction algorithm (or other methodology) may be applied in order to generate images with which a user may interact. Examples of reconstruction algorithms may include those described in one or more of the following U.S. Patents, which are incorporated herein by reference in their entirety: U.S. Pat. No. 8,917,925, entitled "Systems and Methods for Data and Model-Driven Image Reconstruction and Enhancement," issued Dec. 23, 2014, and/or U.S. Pat. No. 10,789,706, entitled "Systems and Methods for Medical Acquisition Processing and Machine Learning for Anatomical Assessment," issued Sep. 29, 2020.

Following reconstruction, image phase 204 may include viewing/manipulating one or more reconstructed image 230, segmenting the reconstructed image 230 to generate an anatomic model 234, and/or preparing an analysis 238 using anatomic model 234. Although singular nouns may be used to describe reconstructed image 230, model 234, and analysis 238, it will be appreciated that such terms, as well as for any other term herein unless otherwise specified, may be singular or plural. Analysis 238 may include, for example, determining/simulating/calculating an $FFR_{CT}$. Analysis 238 may include any type of analysis/interpretation generated according to any suitable type of method. Segmenting the reconstructed image to generate an anatomic model 234 may include any of the techniques of the following U.S. Patents: U.S. Pat. No. 8,315,812, entitled "Method and System for Patient-Specific Modeling of Blood Flow," issued Nov. 20, 2012; U.S. Pat. No. 9,773,219, entitled "Systems and Methods for Using Geometry Sensitivity Information for Guiding Workflow," issued Sep. 26, 2017; U.S. Pat. No. 10,600,181, entitled "Systems and Methods for Probabilistic Segmentation in Anatomical Image Processing," issued Mar. 24, 2020; U.S. Pat. No. 9,304,982; and/or U.S. Pat. No. 9,304,982, entitled "Systems and Methods for Validating and Correcting Automated Medical Image Annotations," issued Apr. 5, 2016.

As shown in FIG. 2, reconstructed image 230 may include artifact(s) 232. Artifact(s) 232 may result from various sources, including from variabilities in any of patient state 210, device properties 212, and/or preparation protocol 214.

Artifact 232 of reconstructed image 230 may be propagated to produce an induced uncertainty 236 (e.g., an induced geometric uncertainty) of anatomic model 234, which may in turn, produce analysis uncertainty 240 of analysis 238. In an example, analysis uncertainty 240 may include an induced $FFR_{CT}$ uncertainty where analysis 238 is an $FFR_{CT}$ analysis.

As shown by the arrow from image phase 204 to acquisition phase 202 and to the arrow representing reconstruction 203, feedback 250 may be utilized. Feedback 250 may be provided at any of the stages of image phase 204 (reconstructed image 230, anatomic model 234, and/or analysis 238). Feedback 250 may be utilized to make adjustments to any aspect of acquisition phase 202 or to a reconstruction process (e.g., a reconstruction algorithm).

Figure 3:
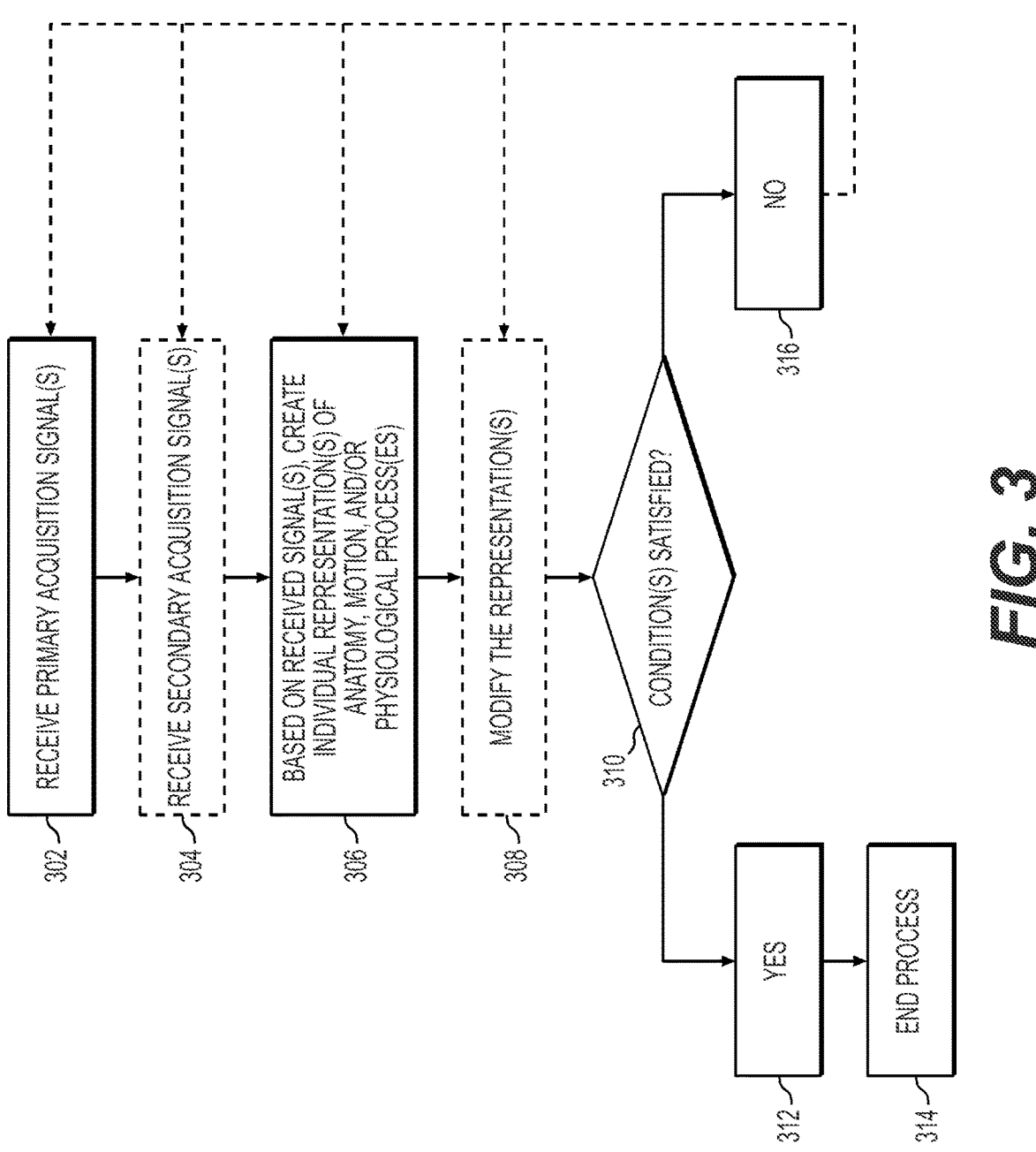
FIG. 3 depicts a flow chart of an exemplary method for creating a physiology-compensated reconstruction.

FIGS. 3-6 depict exemplary methods for physiology-compensated reconstruction. The methods of FIGS. 3-6 are not mutually exclusive, and the steps of the methods may be combined in any suitable combination. FIG. 3 may represent a general example method, and FIG. 4-6 may illustrate particular examples. Each of the methods may be computer-implemented. The steps of the methods described herein are not exclusive; the methods may include additional or alternative step within the scope of the disclosure. Certain embodiments may use known information about latent anatomy and physiology to improve reconstruction of measured anatomy and physiology. Certain reconstruction methods may generally incorporate non-physiological prior knowledge of one or more aspects of the acquisition to ensure mathematical "well-posedness" and improve accuracy.

Method 300 of FIG. 3 may begin with step 302, in which one or more primary acquisition signals are received. The primary acquisition signals may be received in acquisition phase 202, depicted above. The acquisition signals may be acquired using any of the modalities described above, with any of the inputs of acquisition phase 202. Optionally, in step 304, one or more secondary acquisition signals may be received. The secondary acquisition signal(s) may be received from a same measurement modality as the modality producing the signals of step 302 or from a different type of modality. Alternatively, step 304 may be omitted.

In step 306, the received primary acquisition signal(s) and/or secondary acquisition signal(s) (or other input(s)) may be processed into individual representations of one or more of different aspects of the acquisition signal(s), including, for example, anatomy, motion, or one or more physiological processes. In other words, step 306 may identify and process component(s) of the primary and/or secondary signals. Step 306 may utilize known details of a joint representation of an anatomy for which measurements are obtained, motion, and/or physiological processes to decompose the joint representation into individual representations. Step 306 may include using known information about motion, anatomy, and/or physiological processes. Each of a plurality of individual representations generated in step 306 may pertain to a different aspect of the received acquisition signal(s). The known details may arise from manual operator input, from a catalog of information, and/or from machine learning techniques. The known details may be population-based and/or may be patient-specific. In some examples, patient-specific details may be derived from a population-based data source. For example, a machine learning model may be trained based on population-based data, and the trained machine learning model may be applied to a specific patient.

Optionally, in step 308, the individual representations of step 306 may be modified. For example, one or more of a known task, population, physical law, etc. may be used to modify one or more of the representations. In some examples, a trained machine learning model may be utilized to modify the representation. Such modifications may be utilized to address an imaging artifact or other error in the individual representation. In some examples, the modification(s) may correct or compensate for an imaging artifact.

In step 310, it may be determined whether a condition is satisfied. Step 310 may include comparing one or more metrics to a threshold value. If the condition is satisfied in step 312, at step 314 the process of method 300 may be ended and at least one signal may be output. The output signal(s) may include a primary signal related to the received primary acquisition signal in step 302. Additionally or alternatively, the output signal(s) may include a secondary signal related to the received secondary signal in step 304. The output signal(s) may further additionally or alternatively include derivative signal(s) that combine the primary signal(s) received in step 302 and the secondary signal(s) received in step 304. The output signal(s) may include one or more of the individual representation(s) created in step 306 or may aggregate the individual representation(s). The output signal(s) may incorporate the modification(s) of step 308. The output signal(s) may include a reconstruction or may be used to generate a reconstruction of the primary and/or secondary signal(s) received in steps 302 and 304.

If, in step 316, the condition(s) are not satisfied, one or more steps of method 300 may be iterated. The dashed lines of FIG. 3 represent that the iteration may initiate with any of the steps of method 300 and may vary as method 300 further iterates. Further measurements may be acquired (using modified measurement collection parameters, if necessary), further individual representation(s) may be created, and/or further modification(s) may be performed. For example, in a forward model, known details of the measurement acquisition equipment may be utilized to, if necessary, process the original representation(s) created in step 306 or the modified representations(s) created in step 308 into suitable formats, obtain estimates of one or more input signals, compute error with respect to measured input signals, update inputs/representations, and repeat as necessary.

Known information used in step 306 and other steps described herein (including, e.g., step 308) may include various categories of knowledge. The known information described herein additionally or alternatively may be used in other reconstruction steps. For example, information may be known regarding a measurement-gathering system (e.g., imaging system). Such information may include device properties 212. Known information regarding the measurement-gathering system may be used for, for example, model-based iterative reconstruction. For example, known information such as a specification of mathematical models of scanner properties (e.g., geometry, optics, detector response, etc.) may be utilized for iterative reconstruction. Known X-ray physics may be utilized for statistical iterative reconstruction. Such information may include details of x-ray attenuation (e.g., statistical modeling of attenuation measurements via Poisson distribution).

Other types of known information may include known information about the imaged entity (e.g., known details of patient anatomy). Known information of the imaged entity, in some examples, may be utilized for regularized iterative reconstruction. Such prior knowledge may include prior knowledge of measurable anatomy, including, for example, homogeneity of tissue attenuation or composition expressed as total-variation penalty applied to reconstructed intensities. Additionally or alternatively, known-component reconstruction may utilize known information relating to one or more of existence, geometry, or composition of implant hardware (e.g., of a pacemaker device). Further, additionally or alternatively, motion-compensated reconstruction may utilize prior knowledge of measurable physiology, including, for example, specification of a motion model and instantiation thereof for a specific acquisition and/or reconstruction.

Figure 4:
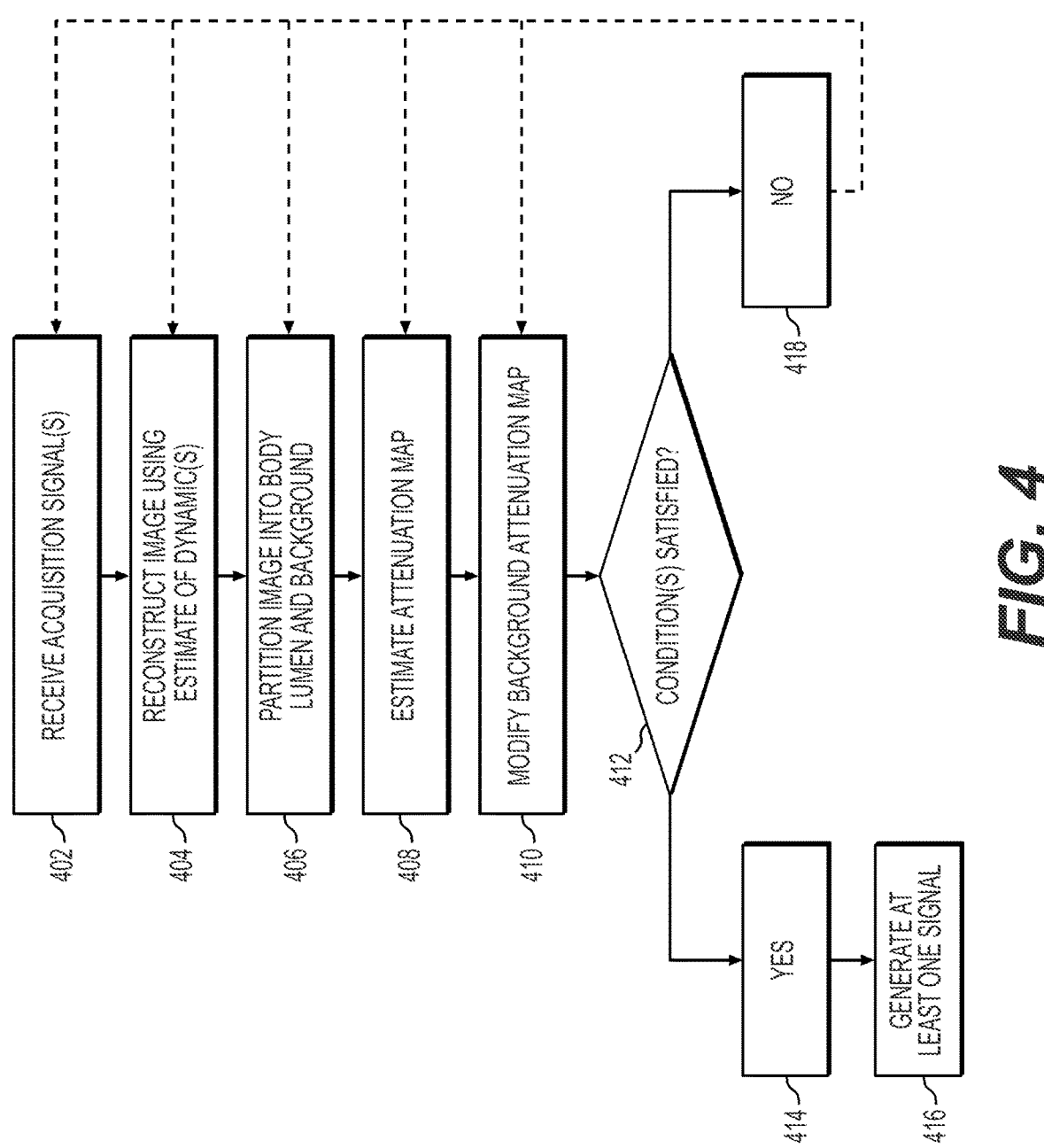
FIGS. 4-6 depict flow charts of exemplary methods for exemplary types of physiology-compensated reconstruction.
Figure 5:
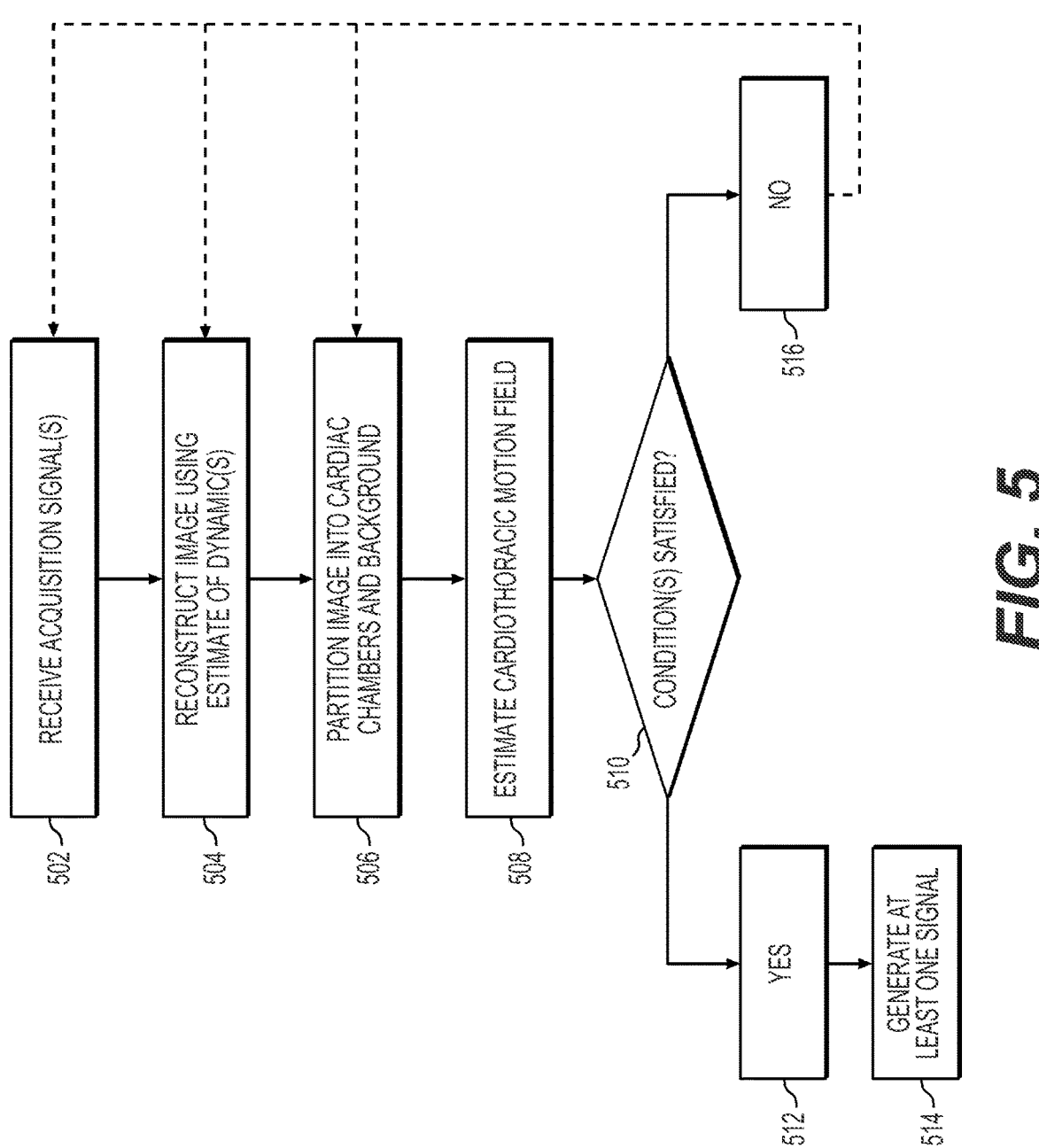
Figure 6:
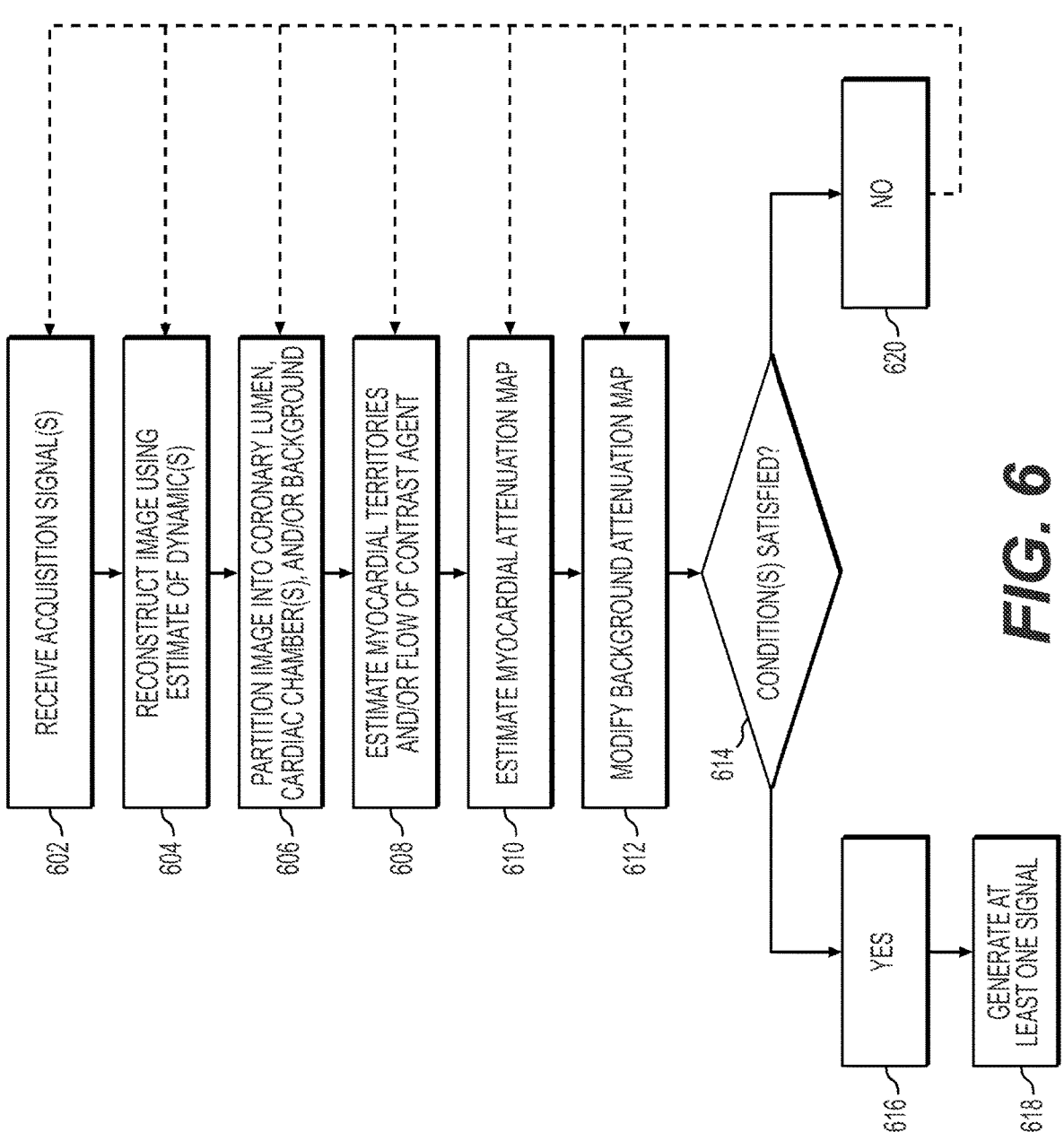

FIGS. 4-6 illustrate exemplary contexts for the systems and methods herein disclosed. In some examples, models of, or physical laws governing, physiological processes may be employed in reconstruction of CCTA images to regularize estimates of anatomical composition and/or motion.

FIG. 4 depicts an exemplary method 400 related to contrast agent transport simulation. In reconstructed CCTA images, contrast attenuation gradients in vessels may encode information about blood flow and/or the morphological impact of disease thereon. This information can be compared with transluminal attenuation gradient (TAG) and/or transluminal attenuation flow encoding (TAFE). Contrast agent transport may be modeled via the advection-diffusion equation. A reconstructed image of contrast-filled vessels may exhibit attenuation values consistent with contrast agent transport. Method 400 may incorporate contrast agent transport simulation to provide consistency, as well as to directly estimate attributes of the dynamic process of interest (e.g., blood flow velocity).

In step 402, one or more acquisition signal(s) may be acquired. Step 402 may include any of the aspects of steps 302, 304, described above. In some examples, the acquired signal may be a sinogram signal. Alternative types of signals may additionally or alternatively be utilized.

In steps 404, and 406, the signal(s) received in step 402 may be processed. In step 404, the image may be reconstructed using a current estimate of dynamics (e.g., vessel dynamics). The dynamics may be estimated using any suitable method. In step 406, the image may be portioned into body (e.g., coronary) lumen(s) and background. The partitioning of step 406 may utilize any known partitioning methods.

Steps 408 and 410 may include modifying the reconstruction of steps 404 and 406. Steps 408 and 410 may include use any of the types of known information described above. Steps 408 and 410 are merely exemplary, and other modification steps may performed within the scope of the disclosure. Step 408 may include estimating an attenuation map, such as a coronary attenuation map. In examples, the coronary attenuation map may be estimated using an advection-diffusion simulation. The simulation domain may include an image partition corresponding to a coronary lumen. In step 410, the background attenuation map may be modified. For example, the background may be optimized using iterative reconstruction techniques. The iterative reconstruction may be used to, for example, fix a coronary attenuation map.

As described below, steps of method 400 may then be iterated, including using any of the iteration steps discussed above. For example, in step 412, it may be determined whether a condition is satisfied. If, in step 414, the condition has been satisfied, the method 400 may be stopped in step 416. An output of method 400 may include data, recommendation(s), action(s), image(s), or any other type of output from a computing device. In step 418, if the condition has not been satisfied, one or more steps of method 400 may be iteratively performed. As discussed above, the dotted lines in the arrows from the iteration step indicate that some, all, or none of the steps may be iterated, and iteration may begin/end at any suitable step. The iteration may continue until the condition in step 418 is satisfied or until method 400 otherwise completes.

FIG. 5 depicts another method 500 related to motion-compensated myocardial perfusion. Reconstructed CCTA images may exhibit motion artifacts across multiple scales due to coronary and/or cardiac motion. Motion artifacts may introduce implausible attenuation values in dynamic structures or structures in close proximity. Such attenuation values may, as shown in FIG. 2, result in proliferated errors in image phase 204. Cardiac motion estimation may be challenging in the presence of severe motion artifacts often observed in reconstructions at non-quiescent cardiac phases. Cardiac motion may be modulated by the electro-mechanics of the heart. A motion-compensated reconstruction method that incorporates an electromechanical simulation of the heart may utilize an ECG acquisition concurrent with image acquisition to estimate cardiac motion.

In step 502, one or more acquisition signal(s) may be acquired. Step 502 may include any of the aspects of steps 302, 304, 402, described above. In some examples, step 502 may include receiving a plurality of signals. One (or ore) of the signals may be a primary signal and one (or more) of the signals may be a secondary signal (as discussed with respect to method 500). Alternatively, each of the received signals may be a primary signal. In some examples, the acquired signal(s) may be a sinogram signal and an ECG signal. Alternative types of signals may additionally or alternatively be utilized.

In steps 504, and 506, the signal(s) received in step 502 may be processed. In step 504, the image may be reconstructed using a current estimate of dynamics (e.g., vessel dynamics and/or cardiac dynamics). The dynamics may be estimated using any suitable method. In step 506, the image may be portioned into cardiac chamber(s) and background. The partitioning of step 506 may utilize any known partitioning methods.

Step 508 may include modifying the reconstruction of steps 504 and 506. Step 508 may include use any of the types of known information described above. Step 508 is merely exemplary, and other modification steps may performed within the scope of the disclosure. Step 508 may include estimating cardiothoracic motion field via electro-mechanical simulation. A simulation domain may include an image partition corresponding to cardiac chambers. Any suitable simulation techniques may be utilized.

As described below, steps of method 500 may then be iterated, including using any of the iteration steps discussed above. For example, in step 510, it may be determined whether a condition is satisfied. If, in step 512, the condition has been satisfied, the method 500 may be stopped in step 514. An output of method 500 may include data, recommendation(s), action(s), image(s), or any other type of output from a computing device. In step 516, if the condition has not been satisfied, one or more steps of method 500 may be iteratively performed. As discussed above, the dotted lines in the arrows from the iteration step indicate that some, all, or none of the steps may be iterated, and iteration may begin/end at any suitable step. The iteration may continue until the condition in step 514 is satisfied or until method 500 otherwise completes.

FIG. 6 depicts another method 600 related to cardiac electromechanical motion simulation. The description of method 500 (or methods 300, 400) also may apply to method 600 in any aspect. Myocardial hypo-attenuation in a territory supplied by a stenosed coronary artery may be indicative of a perfusion defect. However, hypo-attenuation may be obscured by reconstruction artifacts. A reconstruction method that incorporates motion-estimation and territory-estimation may produce a reconstructed image exhibiting increased sensitivity to hypo-attenuation due to perfusion defect(s).

In step 602, one or more acquisition signal(s) may be acquired. Step 602 may include any of the aspects of steps 302, 304, 402, 502, described above. In some examples, the acquired signal may be a sinogram signal. Alternative types of signals may additionally or alternatively be utilized.

In steps 604, 606, and 606, the signal(s) received in step 602 may be processed. In step 604, the image may be reconstructed using a current estimate of dynamics (e.g., vessel dynamics and/or cardiac dynamics). The dynamics may be estimated using any suitable method. In step 606, the image may be partitioned into coronary lumen(s), cardiac chamber(s), and/or background. In step 608, myocardial territories and/or flow of contrast agent thereto may be estimated/simulated.

Steps 610 and 612 may include modifying the reconstruction of steps 604, 606, and 608. Steps 610 and 612 may include use any of the types of known information described above. Steps 610 and 612 are merely exemplary, and other modification steps may performed within the scope of the disclosure. Step 608 may include estimating a myocardial attenuation map via territory modeling and contrast agent concentration evolution. Any suitable estimation method may be utilized. In step 612, a background attenuation map may be modified. For example, the background attenuation may be modified via iterative reconstruction, as discussed below.

As described below, steps of method 600 may then be iterated, including using any of the iteration steps discussed above. For example, in step 614, it may be determined whether a condition is satisfied. If, in step 616, the condition has been satisfied, the method 600 may be stopped in step 618. An output of method 600 may include data, recommendation(s), action(s), image(s), or any other type of output from a computing device. In step 620, if the condition has not been satisfied, one or more steps of method 600 may be iteratively performed. As discussed above, the dotted lines in the arrows from the iteration step indicate that some, all, or none of the steps may be iterated, and iteration may begin/end at any suitable step. The iteration may continue until the condition in step 614 is satisfied or until method 600 otherwise completes.

Any of the exemplary methods and systems disclosed herein may include any of the following aspects, in any combination. Inputs (e.g., inputs of steps 302, 304, 402, 502, 602) may include a sinogram. The sinogram input may include multi-source, multi-detector, multi-energy, and/or longitudinal measurements (or reconstructions thereof). The inputs of 302, 304, 402, 502, and 602 may additionally or alternatively include primary or ancillary acquisitions, such as, for example, ECG, scout films, non-contrast imaging, calcium imaging, and/or any other suitable type of imaging or other measurement).

Any of the simulations described herein (e.g., the simulations of steps 408, 508, 608) may include simulations of cardiac electro-mechanics, contrast agent transport, fluid-structure interaction, and/or solid or deformation mechanics. Any of the reconstructions disclosed herein (e.g., the reconstructions of steps 306, 404, 504, 604) may include reconstructions of cardiothoracic anatomy, such as cardiac chambers, coronary vessels, pulmonary vessels, and/or microvasculature. Any of the reconstructions or simulations may be modified by a presence of implanted hardware.

Figure 7:
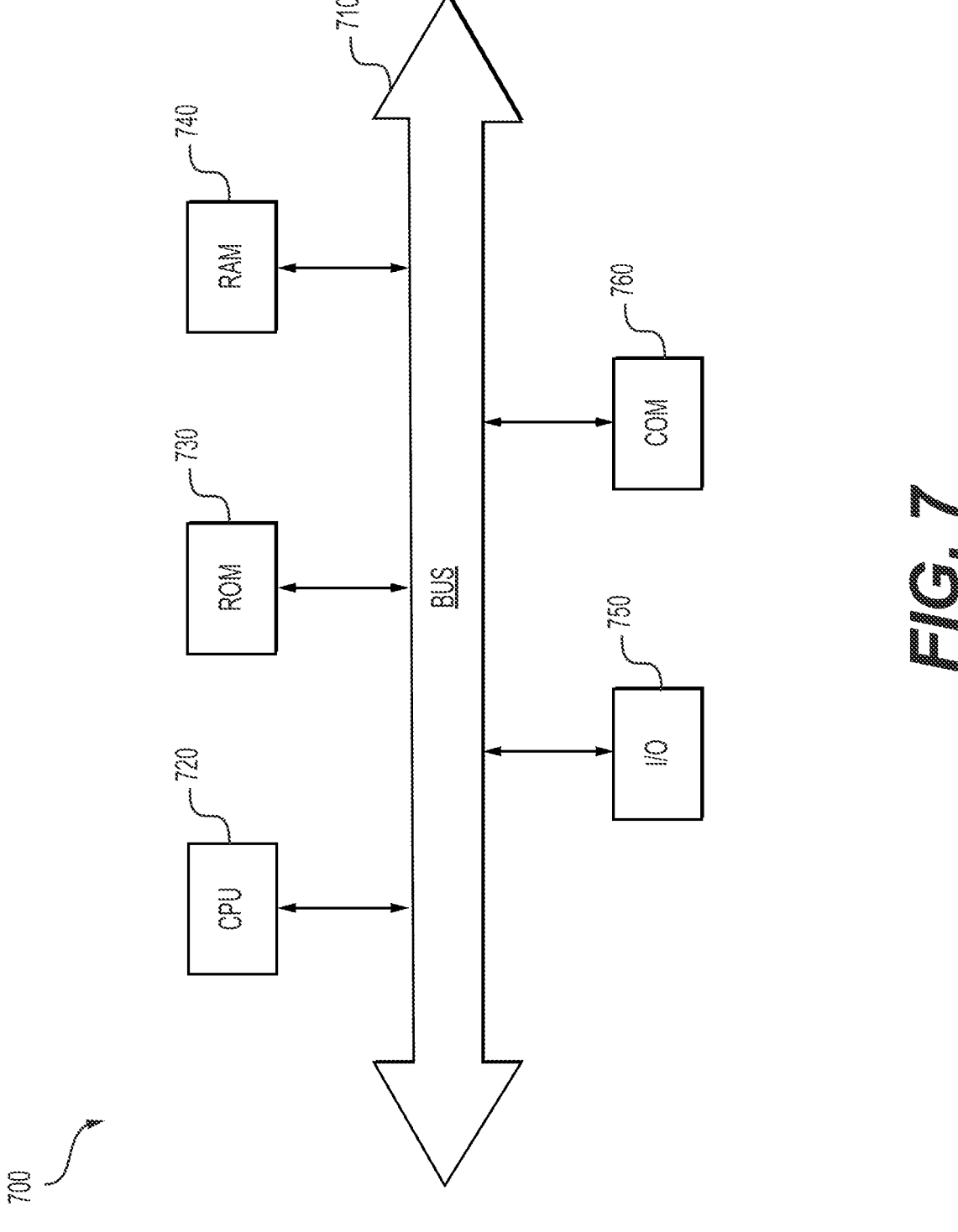
FIG. 7 depicts an exemplary system that may execute techniques presented herein.

As shown in FIG. 7, device 700 may include a central processing unit (CPU) 720. CPU 720 may be any type of processor device including, for example, any type of special purpose or a general-purpose microprocessor device. As will be appreciated by persons skilled in the relevant art, CPU 720 also may be a single processor in a multi-core/multi-processor system, such system operating alone, or in a cluster of computing devices operating in a cluster or server farm. CPU 720 may be connected to a data communication infrastructure 710, for example a bus, message queue, network, or multi-core message-passing scheme.

Device 700 may also include a main memory 740, for example, random access memory (RAM), and also may include a secondary memory 730. Secondary memory 730, e.g. a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 730 may include similar means for allowing computer programs or other instructions to be loaded into device 700. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 700.

Device 700 also may include a communications interface ("COM") 760. Communications interface 760 allows software and data to be transferred between device 700 and external devices. Communications interface 760 may include a modem, a network interface (such as an Ethernet card), a communications port, a PCMCIA slot and card, or the like. Software and data transferred via communications interface 760 may be in the form of signals, which may be electronic, electromagnetic, optical or other signals capable of being received by communications interface 760. These signals may be provided to communications interface 760 via a communications path of device 700, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 700 may also include input and output ports 750 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

One or more techniques presented herein may enable a user, to better interact with a digital image of a glass slide that may be presented on a screen, in a virtual reality environment, in an augmented reality environment, or via some other form of visual display. One or more techniques presented herein may enable a natural interaction closer to traditional microscopy with less fatigue than using a mouse, keyboard, and/or other similar standard computer input devices.

The controllers disclosed herein may be comfortable for a user to control. The controllers disclosed herein may be implemented anywhere that digital healthcare is practiced, namely in hospitals, clinics, labs, and satellite or home offices. Standard technology may facilitate connections between input devices and computers (USB ports, Bluetooth (wireless), etc.) and may include customer drivers and software for programming, calibrating, and allowing inputs from the device to be received properly by a computer and visualization software.

The foregoing general description is exemplary and explanatory only, and not restrictive of the disclosure. Other embodiments of the invention may be apparent to those skilled in the art from consideration of the specification and practice of the invention disclosed herein. It is intended that the specification and examples be considered as exemplary only.

Instructions executable by one or more processors may also be stored on a non-transitory computer-readable medium. Therefore, whenever a computer-implemented method is described in this disclosure, this disclosure shall also be understood as describing a non-transitory computer-readable medium storing instructions that, when executed by one or more processors of a computer system, configure and/or cause the one or more processors to perform the computer-implemented method. Examples of non-transitory computer-readable media include random-access memory (RAM), read-only memory (ROM), solid-state storage media (e.g., solid state drives), optical storage media (e.g., optical discs), and magnetic storage media (e.g., hard disk drives). A non-transitory computer-readable medium may be part of the memory of a computer system or separate from any computer system.

A computer system may include one or more computing devices. If a computer system includes a plurality of processors, the plurality of processors may be included in a single computing device or distributed among a plurality of computing devices. A processor may be a central processing unit (CPU), a graphics processing unit (GPU), or another type of processing unit. The term "computational device," as used in this disclosure, is interchangeable with "computing device." An "electronic storage device" may include any of the non-transitory computer-readable media described above.

What is claimed is:

1. A computer-implemented method for medical measurement reconstruction, the method comprising:
   receiving a measurement acquisition signal, wherein the measurement acquisition signal is acquired from medical imaging;
   based on the received measurement acquisition signal, creating a plurality of representations of the measurement acquisition signal, wherein each of the plurality of representations relates to a different aspect of the measurement acquisition signal;
   modifying one or more of the plurality of representations, wherein the modifying the one or more of the plurality of representations addresses at least one physiology-caused artifact in the measurement acquisition signal caused by at least two of the group of: lumen physiology, attenuation dynamics, cardiac chamber physiology, cardiothoracic physiology, myocardial territory physiology, and flow of a contrast agent; and
   generating an output signal including the modified one or more of the plurality of representations.

2. The computer-implemented method of claim 1, wherein the output signal includes a reconstruction of the measurement acquisition signal or wherein the output signal is used to generate a reconstruction of the measurement acquisition signal.

3. The computer-implemented method of claim 1, wherein the measurement acquisition signal includes a medical imaging signal.

4. The computer-implemented method of claim 1, wherein the plurality of representations include a representation of at least two of anatomy, motion, or a physiological process.

5. The computer-implemented method of claim 4, wherein the plurality of representations are created based on known information about the at least one of the anatomy, the motion, or the physiological process.

6. The computer-implemented method of claim 1, further comprising determining whether a stop condition is satisfied and, upon determining the stop condition is not satisfied, iterating at least one of the receiving, the creating, the modifying, or the generating step.

7. The computer-implemented method of claim 1, further comprising reconstructing an image using an estimate of dynamics.

8. The computer-implemented method of claim 1, further comprising modifying the representation based on a presence of an implanted hardware.

9. The method of claim 1, wherein the plurality of representations of the measurement acquisition signal is created by decomposing the measure acquisition signals.

10. The method of claim 1, wherein modifying the one or more of the plurality of representations includes estimating an attenuation map.

11. The method of claim 1, wherein generating the output signal includes segmenting a reconstructed image to generate an anatomic model and preparing an analysis using the anatomic model.

12. The method of claim 11, wherein the analysis includes determining, simulating, and calculating a fractional flow reserve.

13. A system for processing electronic images for medical measurement reconstruction, comprising:
   a data storage device storing instructions for medical measurement reconstruction; and
   a processor configured to execute the instructions to perform operations comprising:
      receiving a measurement acquisition signal, wherein the measurement acquisition signal is acquired from medical imaging modalities;
      based on the received measurement acquisition signal, creating a plurality of representations of the measurement acquisition signal, wherein each of the plurality of representations relates to a different aspect of the measurement acquisition signal;
      modifying one or more of the plurality of representations, wherein the modifying the one or more of the plurality of representations addresses at least one physiology-caused artifact in the measurement acquisition signal caused by at least two of the group of: lumen physiology, attenuation dynamics, cardiac chamber physiology, cardiothoracic physiology, myocardial territory physiology, and flow of a contrast agent; and
      generating an output signal including the modified one or more of the plurality of representations.

14. The system of claim 13, wherein the output signal includes a reconstruction of the measurement acquisition signal or wherein the output signal is used to generate a reconstruction of the measurement acquisition signal.

15. The system of claim 13, wherein the plurality of representations include a representation of at least one of anatomy, motion, or a physiological process.

16. The system of claim 15, wherein the plurality of representations are created based on known information about the at least one of the anatomy, the motion, or the physiological process.

17. The system of claim 13, the operations further comprising reconstructing an image using an estimate of dynamics.

18. A non-transitory computer-readable medium storing instructions that, when executed by one or more processors, cause the one or more processors to perform operations for medical measurement reconstruction, the operations comprising:
   receiving a measurement acquisition signal, wherein the measurement acquisition signal is acquired from medical imaging modalities;
   based on the received measurement acquisition signal, creating a plurality of representations of the measurement acquisition signal, wherein each of the plurality of representations relates to a different aspect of the measurement acquisition signal;
   modifying one or more of the plurality of representations, wherein the modifying the one or more of the plurality of representations addresses at least one physiology-caused artifact in the measurement acquisition signal caused by at least two of the group of: lumen physiology, attenuation dynamics, cardiac chamber physiology, cardiothoracic physiology, myocardial territory physiology, and flow of a contrast agent; and
   generating an output signal including the modified one or more of the plurality of representations.

19. The non-transitory computer-readable medium of claim 18, wherein the output signal includes a reconstruction of the measurement acquisition signal or wherein the output signal is used to generate a reconstruction of the measurement acquisition signal.

15

16

20. The non-transitory computer-readable medium of claim 18, wherein the plurality of representations include a representation of at least one of anatomy, motion, or a physiological process.

* * * * *